United States Patent
King et al.

(10) Patent No.: US 11,806,276 B2
(45) Date of Patent: Nov. 7, 2023

(54) DEVICE FOR HYPOTHERMIA THERAPY

(71) Applicants: Lucent Medical Systems, Inc., Kirkland, WA (US); University of Miami, Miami, FL (US)

(72) Inventors: Curtis S. King, Kirkland, WA (US); Suhrud Rajguru, Coral Gables, FL (US); Abhishek Prasad, Coral Gables, FL (US)

(73) Assignee: Lucent Medical Systems, Inc., Kirkland, WA (US)

( * ) Notice: Subject to any disclaimer, the term of this patent is extended or adjusted under 35 U.S.C. 154(b) by 461 days.

(21) Appl. No.: 16/925,301

(22) Filed: Jul. 9, 2020

(65) Prior Publication Data

US 2022/0008247 A1     Jan. 13, 2022

(51) Int. Cl.
*A61F 7/12*        (2006.01)
*A61F 7/00*        (2006.01)

(52) U.S. Cl.
CPC ........ *A61F 7/12* (2013.01); *A61F 2007/0002* (2013.01); *A61F 2007/0056* (2013.01); *A61F 2007/0095* (2013.01); *A61F 2007/126* (2013.01)

(58) Field of Classification Search
CPC ...... A61F 2007/0002; A61F 2007/0054; A61F 2007/0056; A61F 2007/0095; A61F 2007/0096; A61F 2007/0228; A61F 2007/0285; A61F 2007/0288; A61F 2007/101; A61F 2007/126; A61F 7/02; A61F 7/12

See application file for complete search history.

(56) References Cited

U.S. PATENT DOCUMENTS 6,106,518 A * 8/2000 Wittenberger ......... A61B 18/02
                                                   606/23
10,271,987 B2   4/2019   Rajguru et al.

* cited by examiner

*Primary Examiner* — Tigist S Demie

(57) ABSTRACT

A device to change the temperature of a localized volume of material. A workable device includes at least one heat transfer mechanism having an external surface for direct contact with an exposed surface of the material. A working fluid is directed by input and output conduits to contact an internal surface of the heat transfer mechanism. The heat transfer mechanism exchanges heat between the working fluid and the material. Temperature of the working fluid may be regulated by a thermal system disposed at a remote location. An optional temperature sensing element may monitor a local temperature of the heat transfer mechanism or otherwise infer a temperature of a portion of the material. Sometimes, a device includes a cooperating anchoring arrangement to facilitate holding the heat transfer mechanism in a desired spot. Certain devices may be plastically deformed to a desired device shape.

15 Claims, 15 Drawing Sheets

DEVICE FOR HYPOTHERMIA THERAPY

STATEMENT AS TO FEDERALLY SPONSORED RESEARCH

This invention was made with government support under DC013798, TR002736, and EB022357 awarded by the National Institutes of Health. The government has certain rights in this invention.

BACKGROUND

Field of the Invention

This invention relates to devices configured to change the temperature of a localized area or volume of material. It is particularly directed to direct contact devices for cooling an exposed surface portion of a medical patient's body to a controllable value having a magnitude of less than a conventional local body temperature.

State of the Art

Therapeutic hypothermia (TH) or lowering of body, spinal cord or brain temperature after a central nervous system (CNS) injury has been used successfully as a neuroprotective intervention for both spinal cord and brain trauma in preclinical models and in humans. Induction of hypothermia prior or after an injury is known to yield favorable neurological outcomes in both the short- and long-terms and these neuroprotective benefits of early hypothermia application minimize secondary inflammatory responses and injuries due to brain trauma, stroke, and spinal cord injury. It is also evident that these neuroprotective beneficial effects are enhanced when cooling is localized in models of both brain and spinal cord trauma. Mild to moderate cooling has been suggested to affect multiple pathways, modulating inflammatory and apoptotic pathways and result in the reduction of free radical production.

The protective effects of mild hypothermia associated with suppression of injury-induced immune responses may be beneficial at countering some of the host responses following electrode implantation. For example, cooling inhibits vasogenic edema formation and the release of fibrinogen and fibronectin, the suppression of polymorphonucleocyte chemotaxis and shows a reduction in gliosis, leading to greater neuronal and axonal preservation. MTH also reduces excitotoxicity by decreasing glutamate release and subsequent NMDA receptor activation leading to cell death. Expression levels of several pro-inflammatory cytokines including tumor necrosis factor alpha and apoptotic factors such as caspases are also reduced with cooling, leading to a significant reduction in the host response. Further, microglial and monocyte activation and infiltration at the injury site is reduced with cooling. Hypothermia can also minimize Blood Brain Barrier (BBB)-disruption by decreasing vascular permeability, edema, and matrix metalloproteinase expression, which are known to degrade the extracellular matrix and consequentially increases inflammation.

In the past decades, intracortical microelectrode arrays have been developed for research, therapeutic and neuroprosthetic applications. These devices working as brain-computer and brain-machine interfaces are intended to benefit patients with nervous system injuries. These devices are implanted in brain, spinal cord or can be implanted in peripheral nerves such as sciatic nerve. Deep brain stimulation (DBS) devices are implanted for treatment of movement related neurological disorders (such as Parkinson's) already. However, their research and clinical utility has been limited by critical barriers such as long-term electrode stability and variable performance.

It has been demonstrated that the function of intracortical microelectrodes is affected greatly by the implantation injury and host tissue responses. Various biological mechanisms including acute and chronic inflammation, oxidative stress, and blood-brain barrier disruption have been shown to contribute to this. Additionally, there is a risk of damage or injury to the nervous system during many neurological surgeries as well as deep brain stimulation. There is an urgent need to develop new approaches to mitigate this injury to the tissue and protect neuronal function.

BRIEF SUMMARY OF THE INVENTION

This invention provides a heat transfer mechanism with an external surface to contact a portion of an exposed surface of a material to effect temperature change on a local portion of the material. Here, the term "local" is used to distinguish over systemic temperature modification. The heat transfer mechanism is desirably transversely flexible to conform to the anatomical surface. Heat transfer into, or out of, the material is primarily by way of conduction. The volume of temperature-regulated material produced by operation of devices according to certain principles of this invention is typically quite small.

An input conduit is placed into fluid communication with the heat transfer mechanism to direct a working fluid toward an internal surface of the heat transfer mechanism. An output conduit is also placed into fluid communication with the heat transfer mechanism to direct the working fluid away from the internal surface of the heat transfer mechanism.

Desirably, the heat transfer mechanism includes a gap between heat transfer contact loci. In that case, and when cooling a material, the gap cooperates with the loci to impart a multi-trough cooling temperature profile to the surface of the material, the temperature profile being disposed at a cross-section taken through the gap. A workable gap may have a size between 0.02 inches and 0.32 inches.

A gap is typically associated with an aperture having a length axis and extending through a thickness of the heat transfer mechanism. Sometimes, an aperture may define a complete perimeter boundary for a temperature-controlled work area. Other times, an aperture may define an incomplete perimeter boundary for a temperature-controlled work area, the incomplete perimeter including a side opening. It is within contemplation that a thermal device may provide a plurality of spaced-apart apertures.

Certain embodiments may include a plastically deformable element to permit a user to impart a desired deformed shape to the apparatus. Embodiments may include a temperature sensing element associated with the heat transfer mechanism to infer the temperature of a local portion of the material. Embodiments may also include a catch element to cooperate with a latching anchor to hold the heat transfer mechanism in a desired operable position.

Sometimes, a body portion of the apparatus includes a bonded stack of thin film polymer layers with a top layer; a channel layer; and a bottom layer; portions of an input channel and an output channel being disposed in the channel layer and between the top and bottom layers. A body portion may further include an outer encapsulating layer, which may include a biocompatible material.

One embodiment forms a thermal device to regulate local temperature of a small volume of material by operating on an exposed surface of the material. A thermal device may include a body formed from bonded thin layers of polymer material. Body layers include a top layer, a channel layer, and a bottom layer. The body has an input channel with an input channel length axis disposed in the channel layer, the input channel being defined in part by walls provided by the channel layer, the top layer, and the bottom layer. The body also has an output channel with an output channel length axis disposed in the channel layer, the output channel being defined in part by walls provided by the channel layer, the top layer, and the bottom layer.

A heat transfer mechanism is coupled to, or carried by, the body. A workable heat transfer mechanism includes an aperture to form a gap between heat transferring elements to impart a multi-trough cooling profile to an object that is cooled by the heat transfer mechanism. Sometimes, the aperture includes a closed perimeter to define a fully bounded conduit extending in a transverse direction through the thickness of the heat transfer mechanism. In other cases, the aperture may include a side opening to define a partially bounded conduit extending in a transverse direction through the thickness of the heat transfer mechanism.

A workable thermal device may include an outer encapsulating layer disposed to cover a portion of the body. Desirably, the encapsulating layer is, or includes, a biocompatible material. Embodiments may include a thermal sensor disposed to indicate a temperature associated with the heat transfer mechanism. The indicated temperature may then be used to infer a local temperature of the material. Preferably, a catch element is included to facilitate holding the heat transfer mechanism in a desired location. Also, a plastically deformable member may be associated with the body to permit a user to modify a shape of the body.

The invention may be embodied in a method to perform hypothermia therapy on an animal. One such method includes: exposing a surface of tissue; providing a heat transfer mechanism comprising a bonded stack of thin film layers comprising a top layer, a channel layer, and a bottom layer, an input channel and an output channel with length axes disposed in the channel layer to convey a thermal fluid from a remote fluid temperature management device for wetted contact between the thermal fluid and a heat transfer element; applying the heat transfer mechanism to the surface of tissue to impose a multi-trough cooling profile on the surface of tissue; passing a medical device through an aperture extending through a thickness of the heat transfer mechanism to install the medical device in registration with respect to the tissue; and removing the heat transfer mechanism from the surface. That method may further include removing the heat transfer mechanism by displacing the aperture in a transverse direction relative to the length axis of a wire connected on one end to the medical device to cause the wire to pass through a side opening in the perimeter of the aperture and thereby free the wire from disposition inside the aperture.

BRIEF DESCRIPTION OF THE DRAWINGS

In the drawings, which illustrate what are currently considered to be the best modes for carrying out the invention.

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of certain principles of the present invention, and should not be viewed as narrowing the claims which follow.

Figure 1:
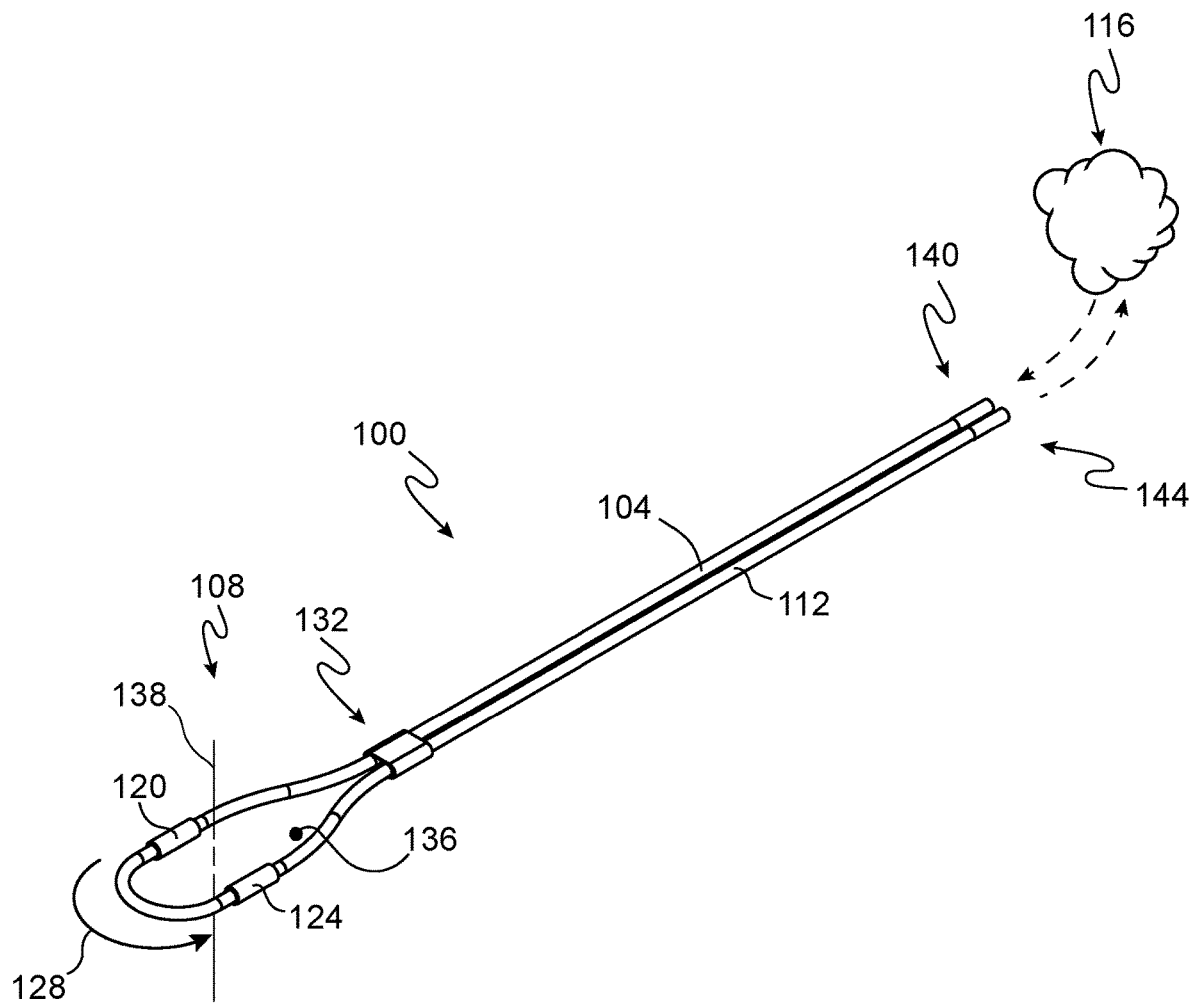
FIG. 1 is a view in perspective of an embodiment according to certain principles of the invention.

An embodiment according to certain principles of the invention is illustrated generally at 100 in FIG. 1. Embodiment 100 is a device to change and desirably regulate the temperature of a local volume of material. For purpose of this disclosure, a device such as thermal device 100 will generally be made reference to as a cooling device. However, it is to be understood that a device, such as illustrated at 100, may find equal utility as a heating device. Other workable devices may be regarded as thermal regulating devices, and may be capable of heating or cooling, or alternating between the two. Certain currently preferred devices described herein are applied to cooling local volumes of tissue, including living animal tissue. Consequently, this disclosure will generally make reference to the thermally regulated material as tissue. It is to be understood that thermal devices according to certain principles of the invention may be applied as well to alternative substrates.

Device 100 includes an input conduit 104 to deliver thermal transfer fluid from a source toward a heat transfer area, generally 108. An output conduit 112 delivers the thermal transfer fluid to a sink. Workable conduits 104, 112 may be formed from sections of fluid-holding tubing, such as medical grade silicone tubing, polymeric tubing, or other suitable hose structure. An exemplary source and sink are indicated generally at 116, and may include a commercially available remote chiller (or heater) to place the thermal fluid at a desired temperature prior to circulation.

Illustrated heat transfer area 108 includes a first heat transfer element 120, and a second heat transfer element 124 that are coupled in fluid communication to conduits 104, 112 such that circulation 128 of the thermal fluid is permitted without leaking. Desirably, a heat transfer element 120, 124 provides a relatively larger thermal conductivity than provided by the delivery conduits 104, 112. A workable heat transfer element 120, 124 may be formed from or include a metal, or metallic material, disposed between the circulating thermal fluid and a tissue or other material.

The preferred arrangement of thermally conductive materials tends to focus any increase in temperature of the circulating thermal fluid to be as a consequence of heat transfer from the desired volume of tissue that is operated on by the device 100. That is, preferred devices extract heat from the tissue for which temperature regulation by heat transfer area 108 is desired. Various ways to infer temperature of the cooled tissue volume are facilitated by selection of desirable constituent materials of a device, such as device 100.

Figure 2:
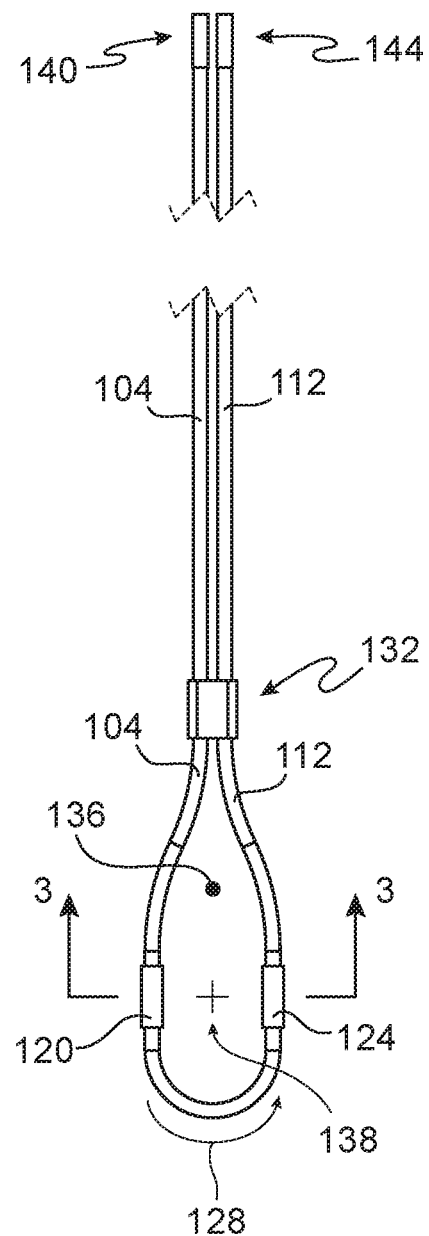
FIG. 2 is a plan view of the embodiment of FIG. 1.

With reference to FIGS. 1 and 2, device 100 includes a connector, generally 132, to form a circulating loop, or aperture 136, for disposition in the heat transfer area 108. Of note, aperture 136 has a length axis 138 that is disposed in penetration through a thickness of the device 100. Also, connectors 140, 144 may be provided for routing thermal fluid conduits to a remote source/sink device 116.

Figure 3:
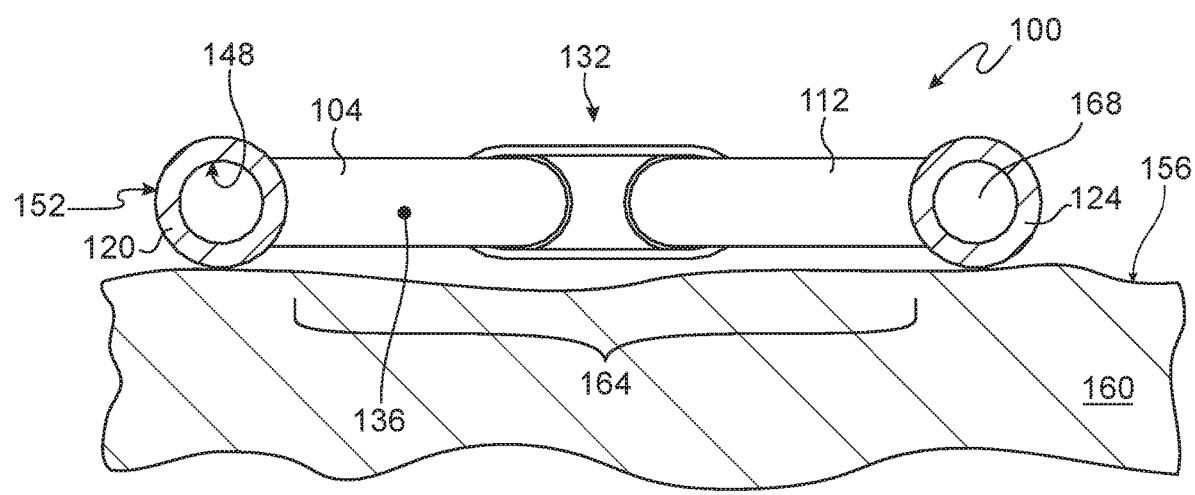
FIG. 3 is a cross-section view indicated at section 3-3 in FIG. 2, and looking in the direction of the arrows, when the device is disposed in operable registration on a tissue surface.

Reference will now be made to FIGS. 2 and 3. A plurality of plumbing connections may be envisioned to place heat transfer elements 120, 124 in leak-tight registration with thermal fluid conduits 104, 112. It has been found workable to make an adhesive butt joint connection between lengths of copper tube and silicone tube. A workable adhesive includes cyanoacrylate. An alternative fluid-tight joint between elements may be welded, molded, adapted for a plug-fit, or in alternative well known ways.

Materials of construction for any constituent element of an embodiment of a device may be selected for reasons of serviceability or compatibility of a thermal device, e.g., device 100, when employed in a particular environment. For example, a thermal element, fluid conduit and/or connector may be formed from a suitable, e.g., inherently biocompatible, material. A biocompatible surface treatment may sometimes be applied to portions of a device. For example, a gold film was applied to exterior contact surfaces of the copper thermal elements 120, 124 of an embodiment used during brain surgery performed on an animal. As one alternative example, a portion of a thermal device may be encapsulated within a biocompatible material, such as is illustrated in e.g., FIG. 5.

In the case particularly illustrated in FIG. 3, thermal fluid may directly contact the inner surface 148 of e.g., a heat transfer element 120. Further, an external surface 152 of a heat transfer element 120 may come into direct contact with a surface 156 of tissue 160 when a device is deployed. As referenced above, the relatively low thermal resistance of a metal heat transfer element facilitates heat transfer from tissue 160, through heat transfer elements, and into thermal fluid 168 circulating 128 in the device 100.

A distance or gap 164 may be defined by a spacing between heat transfer elements (such as elements 120 and 124 in FIGS. 1-3), with the thermal elements being disposed on opposite sides of the aperture 136 in the case illustrated in FIG. 3. It is preferred for the gap 164 to provide a suitably-sized work area of hypothermic tissue surface on which to perform some sort of therapy, invasive interrogation, medical procedure, or the like. A workable gap 164 may be between about 0.020 in-0.315 in [0.5 mm-8 mm], although much larger gaps 164 are within contemplation. The work area provided by the gap 164 in a thermal device such as device 100 may be round, rectangular, or any other convenient shape.

Figure 4:
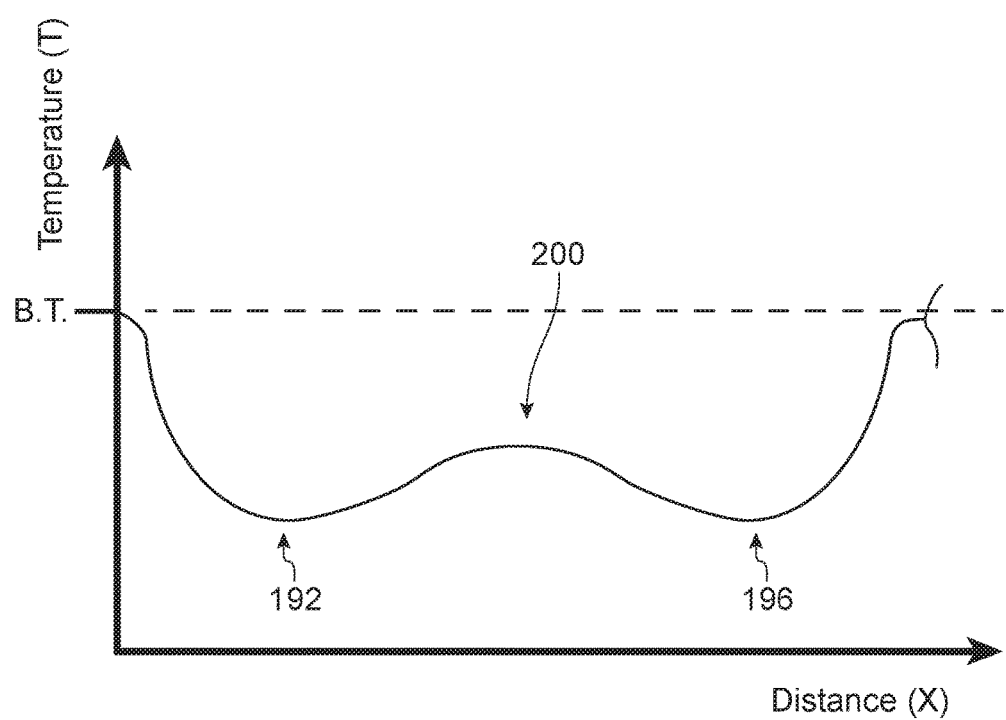
FIG. 4 is an XY plot illustrating a representative surface temperature that may be caused by the embodiment in FIG. 3.
Figure 23:
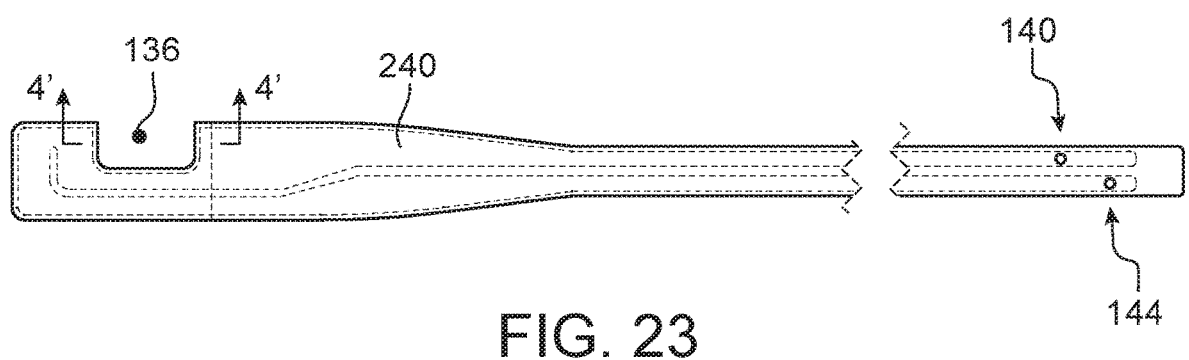
FIG. 23 is a bottom plan view of the embodiment in FIG. 20.
Figure 24:
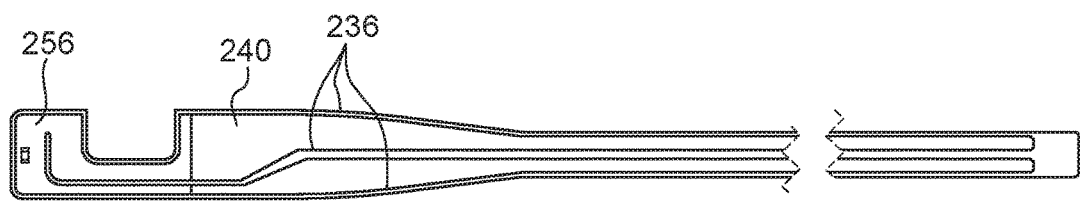
FIG. 24 is a plan view of the embodiment in FIG. 20 at a stage of partial assembly.
Figure 25:
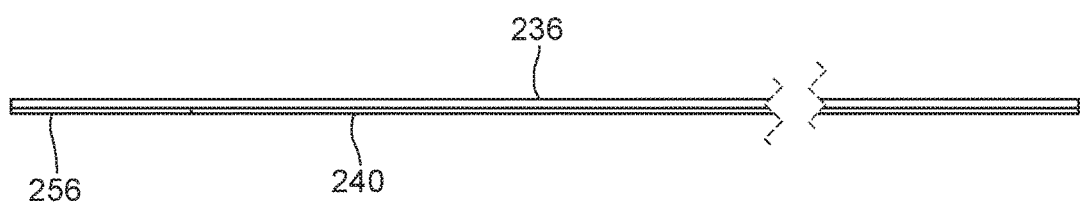
FIG. 25 is a side view of the embodiment in FIG. 24.

The X-Y plot illustrated in FIG. 4 is representative of a surface temperature profile that might be caused by the embodiment and frame of visual reference in FIG. 3. A distance axis X is defined in FIG. 3, and temperature of the surface 156 of the tissue 160 is shown as a cartoon line plot in FIG. 4. The surface temperature permits one to infer the reduced temperature (below the baseline temperature BT) of a local volume of tissue 160 near the device 100. (A similar plot would be expected for the device illustrated in FIG. 23, and indicated by section 4'-4'). In either case, the surface temperature profile is disposed at a cross-section taken through a gap between heat transferring elements.

FIG. 4 illustrates a hypothetical thermal profile of surface temperature at a section through the device 100 operating in a cooling mode. In FIG. 4, temperature at the locus of contact for heat transfer element 120 is generally indicated at 192, and defines a first trough. Similarly, temperature at the locus of contact for heat transfer element 124 is generally indicated at 196, and defines a second trough. The peak generally indicated at 200 represents the maximum surface temperature in the gap 164 (FIG. 3) between the heat transfer element loci. Temperature of material in a volume proximate the device 100 may be inferred from the surface temperature closest to a point of interest inside the volume. That is, one would expect the temperature of tissue to trend toward an undisturbed (e.g., normal or baseline) value with increased distance inside the material and away from a surface-contacting heat transfer element.

FIG. 4 illustrates the general thermal profile of surface temperature expected at a section through the device 100, in which a pair of troughs 192, 196 separated by a peak 200 are illustrated. In contrast, a heat transfer device providing essentially a point source for heat removal (e.g., no gap 164 or aperture corresponding to aperture 136) would be properly illustrated by a curve of surface temperature having a single trough and no separating peak corresponding to peak 200 shown in FIG. 4.

Figure 5:
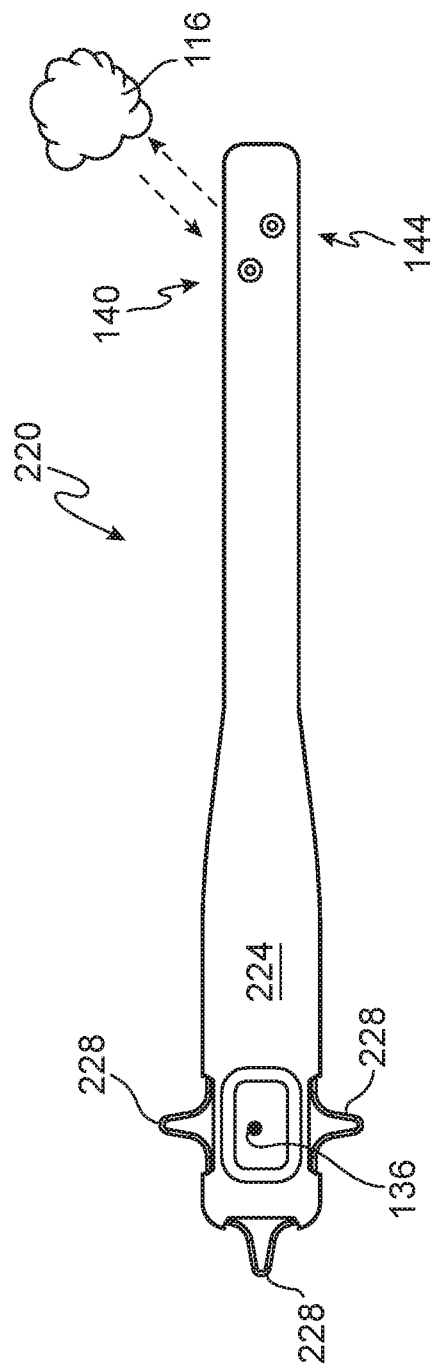
FIG. 5 is a top plan view of a device constructed according to certain principles of the invention.
Figure 16:
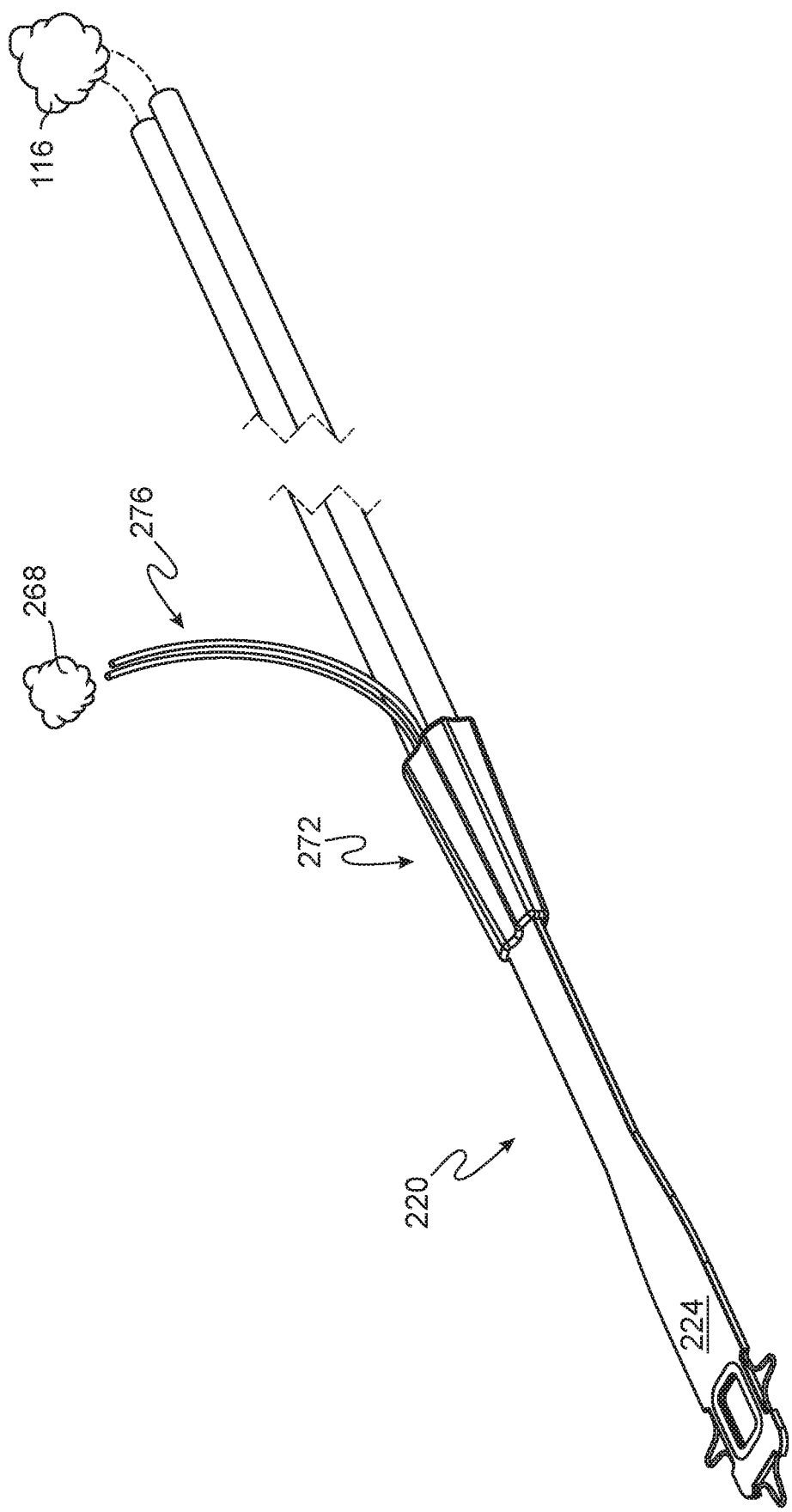
FIG. 16 is a view in perspective of the embodiment in FIG. 5 disposed for connection to ancillary equipment and use in thermal therapy.
Figure 17:
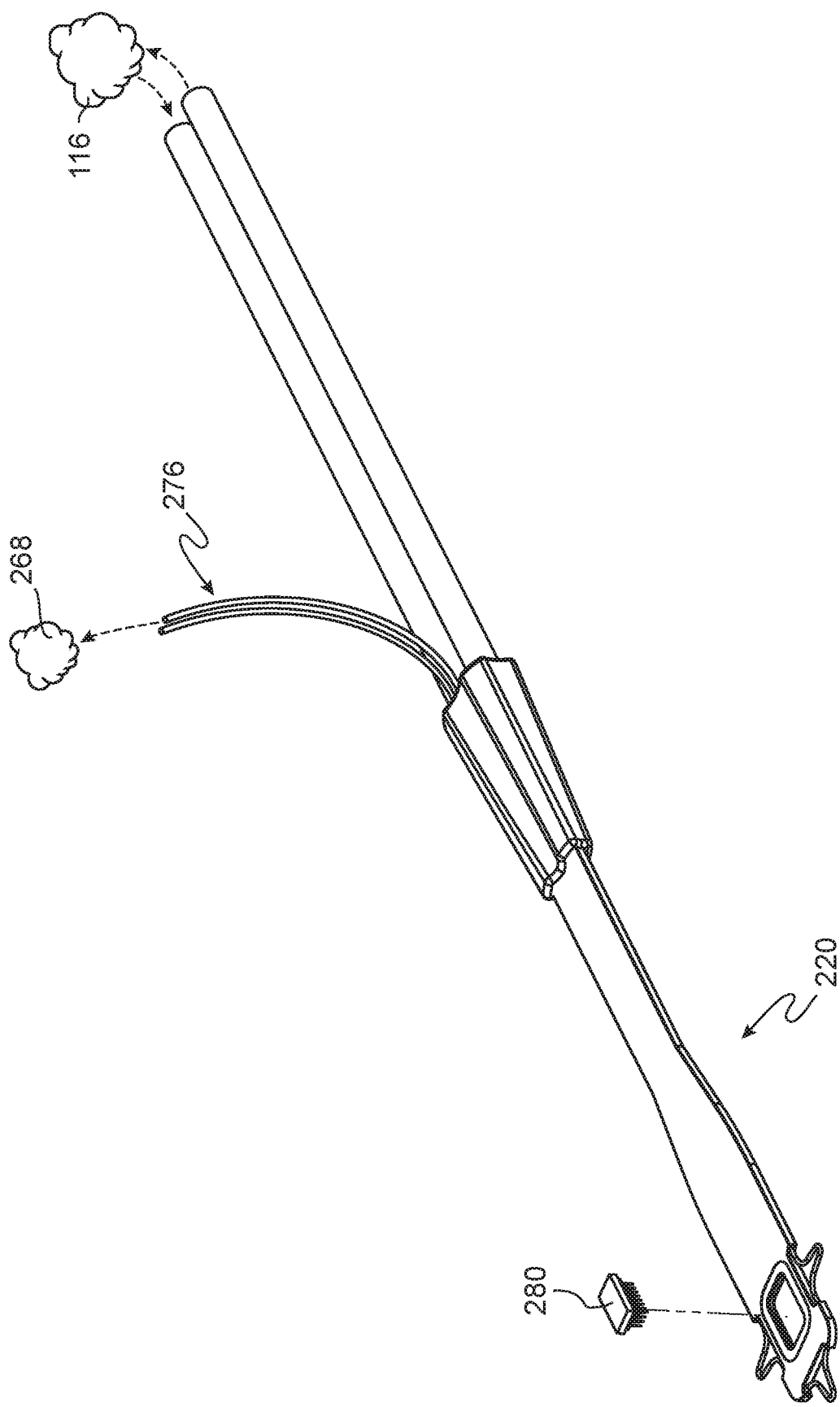
FIG. 17 is a view in perspective of an embodiment coupled to ancillary equipment and ready for deployment as a thermal device.
Figure 19:
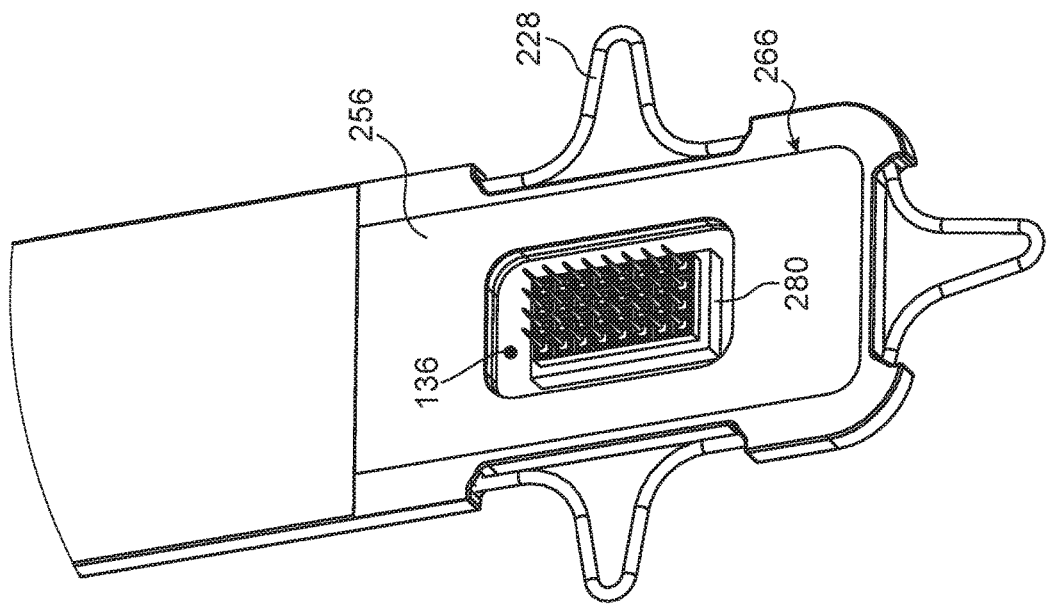
FIG. 19 is a close-up view of a portion of the embodiment in FIG. 18.
Figure 18:
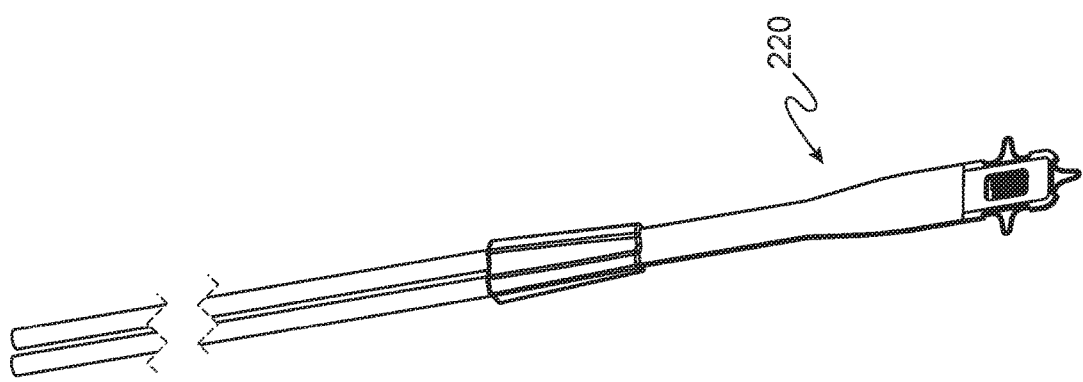
FIG. 18 is a view in perspective of an embodiment associated with an implantable array of electrodes.

An embodiment according to certain principles of the invention is illustrated generally at 220 in FIG. 5. FIGS. 6-16 illustrate details of construction for the embodiment in FIG. 5 and certain related devices. Certain of the latter group of FIGs. may illustrate one or more optional element that may be added to, or redacted from, other embodiments. FIGS. 17-19 illustrate deployment for a preferred use of an embodiment according to certain principles of the invention. FIGS. 20-26 illustrate structural details of another embodiment. Similar elements in different FIGs. are generally annotated with the same, or a modified version of the same, numeral to avoid redundancy of disclosure. Because a preferred use of certain embodiments is to apply hypothermia therapy to living tissue, a device may be made reference to in this disclosure as a thermal- or thermal therapy device.

With reference again to FIG. 5, thermal therapy device 220 includes a body 224 with a portion defining a through-hole or aperture 136. In the illustrated top view, it may be visualized that aperture 136 forms a complete boundary extending around a perimeter of a temperature-controlled work surface, where the work surface can be accessed through the aperture 136.

One or more catch element 228 may sometimes be provided to facilitate holding the aperture 136 in registration at a desired position. Desirably, a catch element cooperates with a latch element to hold a heat transferring portion of a thermal therapy device in operable registration to apply a localized thermal therapy to a portion of tissue. An exemplary latch element may include a screw affixed to bone. The screw may be essentially lassoed by a catch 228. One alternative includes a suture placed in cooperation through a catch loop and adjacent tissue to hold a heat transfer area in registration with respect to tissue. Other cooperating catch and latch structures will occur to one of ordinary skill in the art.

Figure 6:
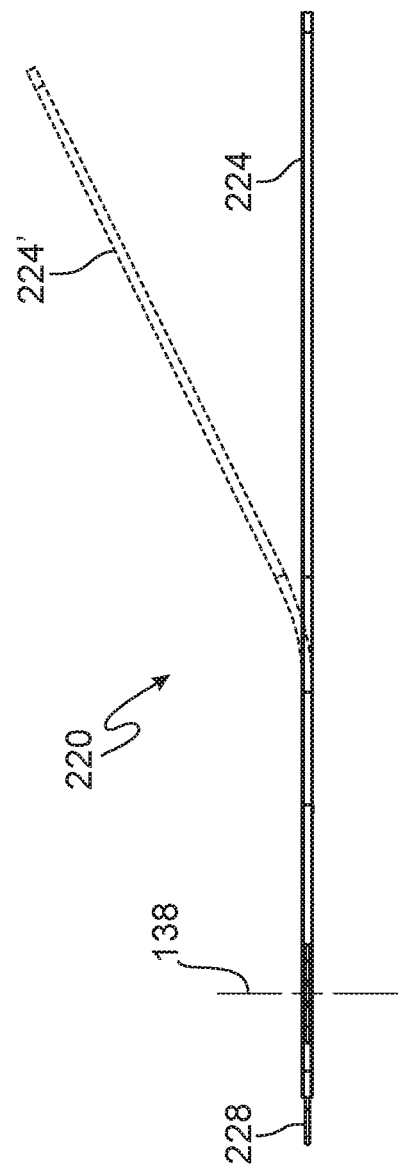
FIG. 6 is a side view in elevation of the device in FIG. 5.
Figure 13:
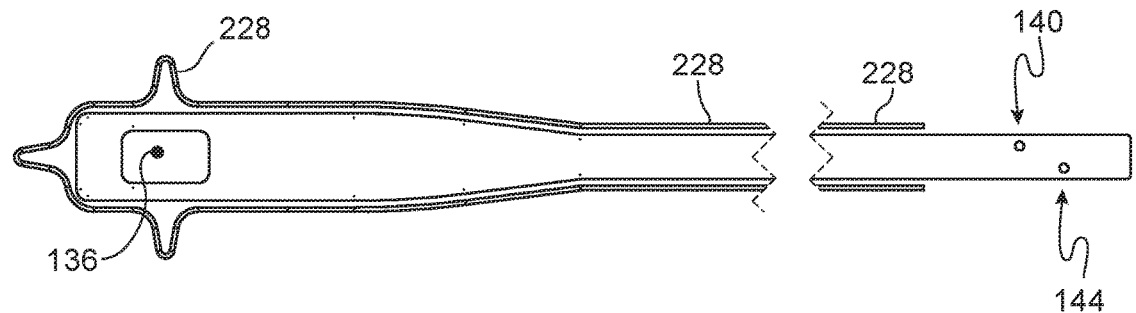
FIG. 13 is a plan view of the embodiment in FIG. 11, at a further stage of assembly.
Figure 14:
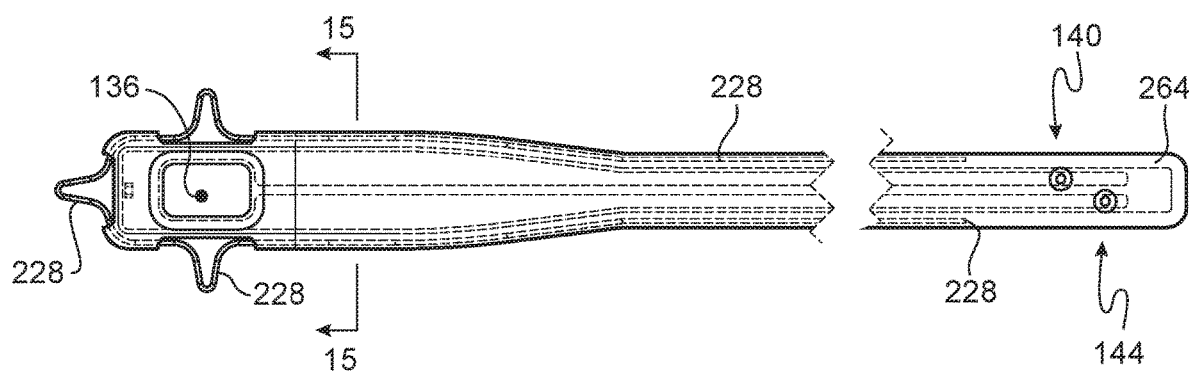
FIG. 14 is a plan view of the embodiment in FIG. 13, at a further stage of assembly.

As illustrated in FIG. 6, sometimes a thermal device may be configured to permit a user to plastically deform a portion of the device from a first configuration (e.g., the solid line portion 224 in FIG. 6) to a second configuration (e.g., dashed line portion 224' in FIG. 6). One construction to accomplish a plastically deformable portion includes length extensions of one or more catch element along the length of a device. As best illustrated in FIGS. 13, 14, and 16, a workable catch element 228 may include a length of malleable wire including a length extending along a length axis of body 224. A similar functionality may be provided by a dedicated deformable element, e.g., a fully or partially embedded malleable length of wire lacking a catch portion or other functionality. A workable deformable element may be composed of, or include stainless steel, titanium, other metals, and the like. It is within contemplation that a shaped memory alloy may also be incorporated in a system to deform a thermal device, such as device 220, as a function of temperature.

Connector elements 140, 144 are provided to couple thermal fluid from a source 116 to internal fluid channels or conduit elements defined within the body 224. Channels or conduit elements may conveniently be formed inside a body 224 formed from a plurality of layers of membrane sheets or films. Workable membrane material includes polymer membranes, such as thin sheets or films of polypropylene, Mylar, and the like. Layer thickness for each layer in a laminate style thermal therapy device 220 may range from 0.001 in-0.010 in [0.025 mm-0.254 mm]. Such materials are inherently flexible in a direction transverse to the planar width and length axes.

Certain layers may inherently carry surface adhesive, or sometimes, adhesive may be applied as separate layers between film layers. Layers may be transparent or opaque. Certain layers may be metallized or metallic. Portions of a layer may be formed from different materials, and constituent materials of a layer may be overlapped at an edge, or butt jointed. Therefore, a layer may not be uniform in thickness throughout. Desirably, a multilayer body retains a certain amount of transverse flexibility to permit conformability of a heat transfer surface to a surface of tissue undergoing therapy.

Different portions may be selectively removed from certain layers to form a built-up stack of layers having internal structures, including the aforementioned fluid conduits. For example, individual film layers may be die- or laser-cut, and stacked to form a composite multilayer body. This can be performed in a reel-to-reel process, with portions of individual bodies 224 being extracted from formed and bonded layers of a multilayer ribbon of material that defines a series of bodies, or portions thereof. Alternative manufacturing methods to create bodies having internal structures nonexclusively include: photolithography; etching, and machining including micromachining.

Figure 12:
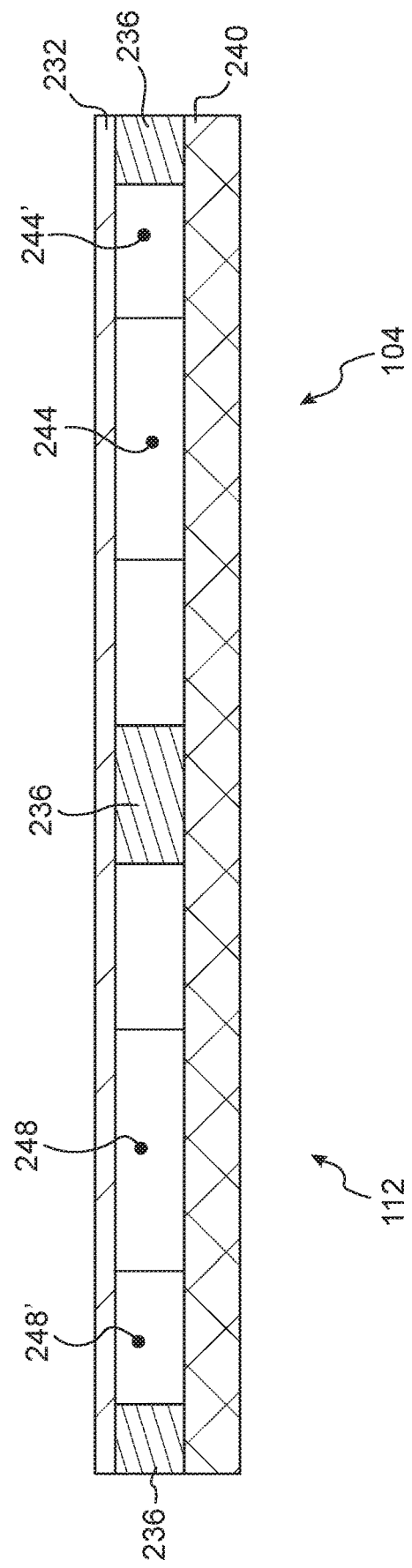
FIG. 12 is a cross-section view indicated at section 12-12 in FIG. 11 and looking in the direction of the arrows.

With reference to FIG. 12, a body 224 may include a cap sheet or layer 232 bonded to a channel layer 236, which is in turn bonded to a floor sheet or layer 240. The input lumen 244 of an input conduit, generally 104, is bounded by top sheet 232, walls in channel layer 236, and a floor provided by floor layer 240. The narrowed-down portion 244' of input lumen 244 is located at one side of aperture 136 (see FIG. 11). Similarly, output lumen 248 of an output conduit, generally 112, is bounded by top sheet 232, walls in channel layer 236, and a floor provided by floor layer 240. The narrowed-down portion 248' of output lumen 248 is located at the other side of aperture 136.

Figure 7:
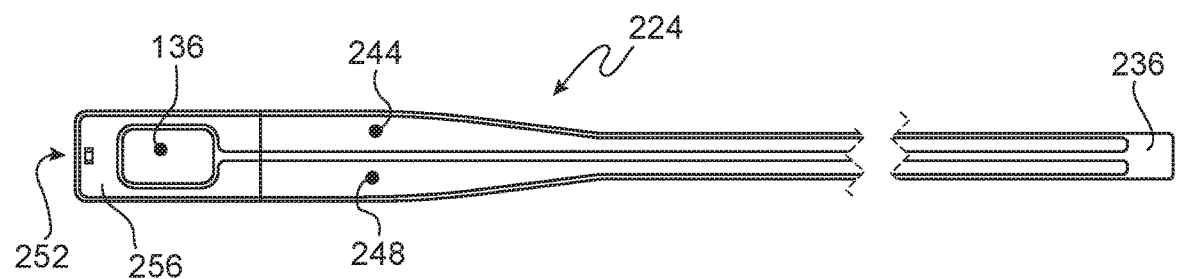
FIG. 7 is a top view of the device in FIG. 5, partially assembled with the top layer removed.
Figure 8:
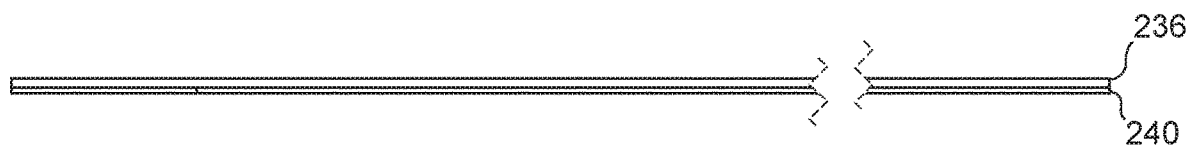
FIG. 8 is a side view of the embodiment in FIG. 7.
Figure 9:
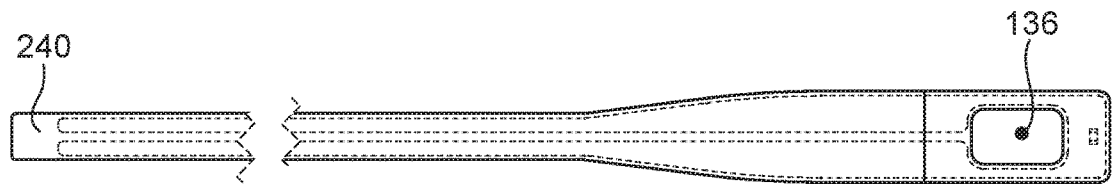
FIG. 9 is a bottom plan view of the embodiment in FIG. 7.
Figure 10:
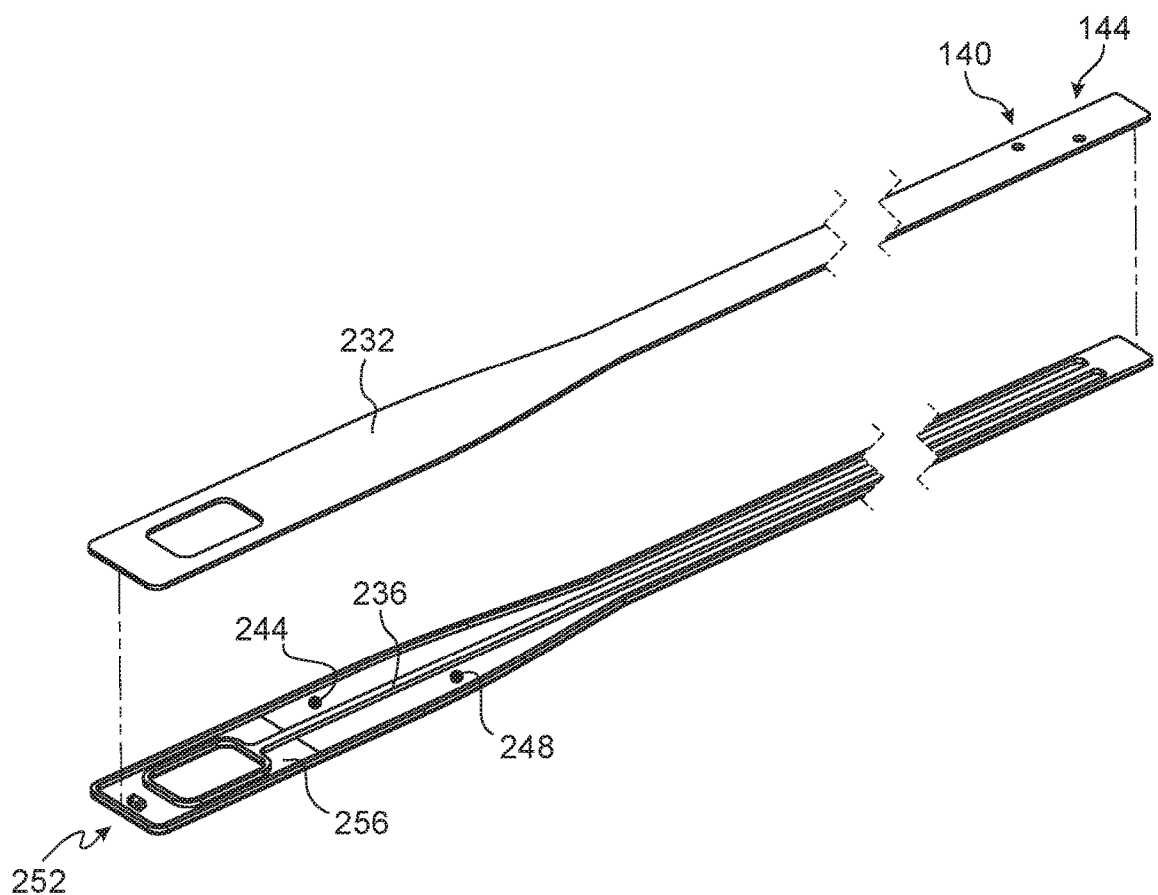
FIG. 10 is an exploded view in perspective of a portion of the embodiment in FIG. 5, partially assembled.
Figure 11:
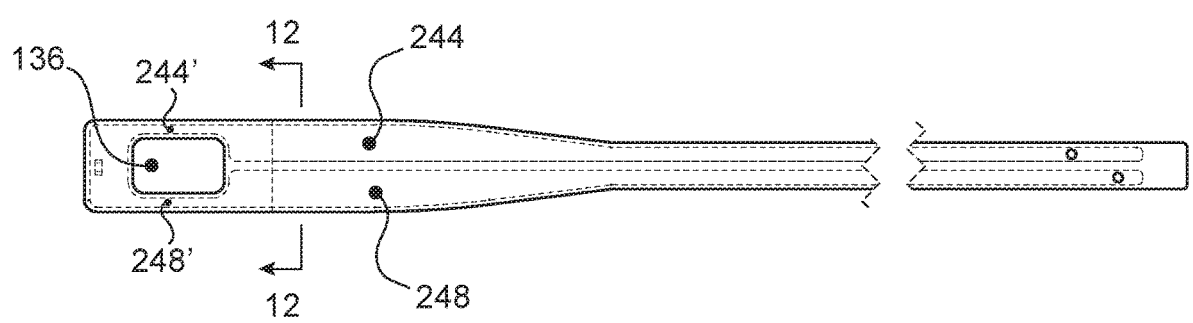
FIG. 11 is a top view of the embodiment in FIG. 10, at a further stage of assembly.

FIG. 7 illustrates an embodiment 220 in a state of partial assembly. As illustrated, top layer 232 is removed, and internal features of the body, generally indicated at 224, are visible. It may be seen that channel layer 236 forms side walls for input lumen 244 and output lumen 248, as well as a fluid resistant wall around a portion of aperture 136. While optional, a thermal indication element or sensor 252 is desirably included, and is preferably placed in contact with a heat transfer element 256. A workable thermal sensor 252 nonexclusively includes a thermistor, thermocouple, and the like. Heat transfer element 256 is illustrated as being butt-jointed with a portion of polymeric film to form part of a multi-component floor layer 240. As previously mentioned, it is preferred for a heat transfer element, such as floor portion 256, to possess high thermal transmission capability.

Sometimes, it is helpful to measure the temperature of floor portion 256 (e.g., the heat transfer element that is expected to be in contact with tissue). Accurate knowledge of the floor temperature lends accuracy to the surface temperature of the tissue at the contact loci, and consequently improves accuracy of the inferred temperature in a local volume of tissue. In an alternative arrangement, temperature of the returning thermal fluid may be used to provide estimated floor temperature.

Figure 15:
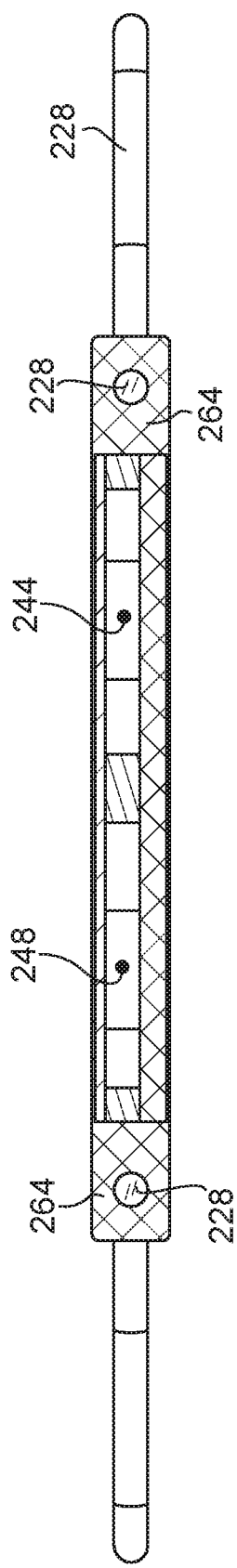
FIG. 15 is a cross-section view indicated at section 15-15 in FIG. 14 and looking in the direction of the arrows.

As illustrated between FIGS. 13-15, sometimes, an embodiment may include an encapsulating coating or layer 264. In that case, it is typically desirable to pull the edge of the layer 264 back from the edges of certain structures, such as aperture 136 and connector structures 140 and 144, as illustrated in e.g., FIG. 14. Another example is illustrated in FIG. 19, where perimeter boundary 266 is pulled back from a heat transferring portion 256 of floor 240. It should be noted that a body may extend by any desired distance in a length direction, as also indicated in FIG. 14.

FIG. 16 illustrates a thermal device 220 in position to couple with ancillary equipment, such as a source/sink 116 and a temperature display system 268. As illustrated, a connector/manager element, generally 272, is coupled to a body 224. Connector/manager element 272 may include coupling structure to cooperate with elements 140 and 144 to place source/sink 116 into fluid communication with input lumen 244 and output lumen 248. Further, manager element 272 may couple leads, generally indicated at 276, from a temperature sensor 252 or other device carried on-board a body 224.

FIGS. 17-19 illustrate details of use of a currently preferred embodiment in an exemplary application to apply controlled hypothermia therapy during installation of an individually addressable multi-electrode assembly 280 into brain tissue of a mammal. The thermal device 220 is first used to cool a small volume of a local exposed surface portion of brain tissue, and the electrode array 280 is stabbed through aperture 136 and into registration on the exposed surface of the brain tissue. The temperature of the small local volume of brain tissue is regulated to remain at a reduced temperature (e.g., below a baseline or normal temperature), for a period of time to reduce trauma to the tissue. Wires may be attached to one or more electrode of the electrode array 280, and the brain may be probed while the local volume of brain tissue remains at a reduced temperature. Sometimes, the thermal device 220 is removed, but brain probing may continue. Wires passing through the aperture 136 can be problematic, and may need to be temporarily disconnected to remove the thermal device 220.

Figure 20:
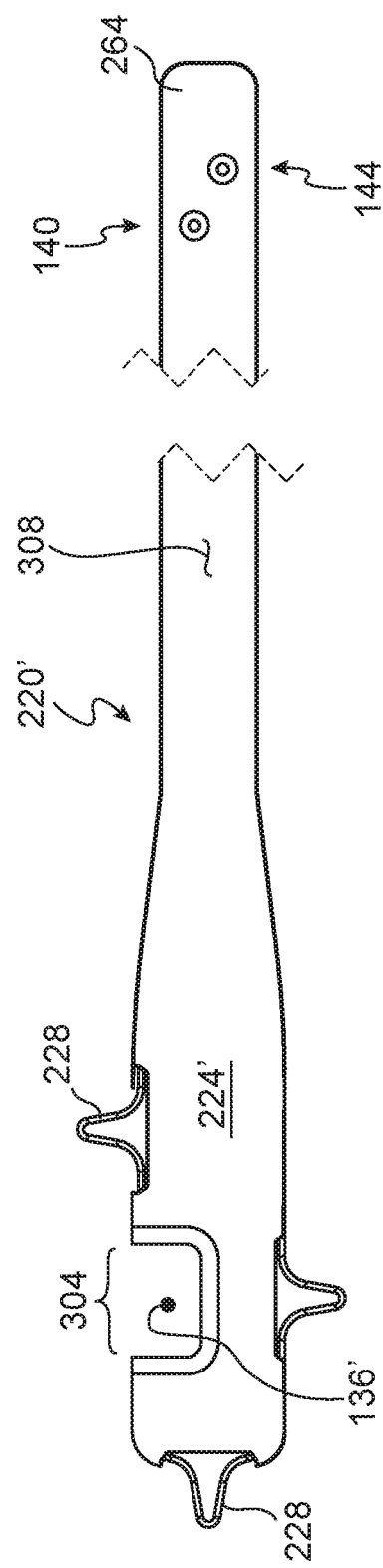
FIG. 20 is a top plan view of an embodiment.
Figure 21:
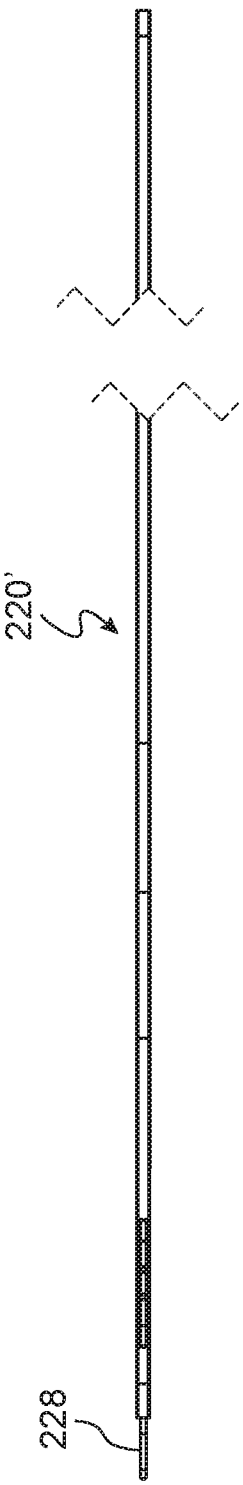
FIG. 21 is a side view of the embodiment in FIG. 20.
Figure 22:
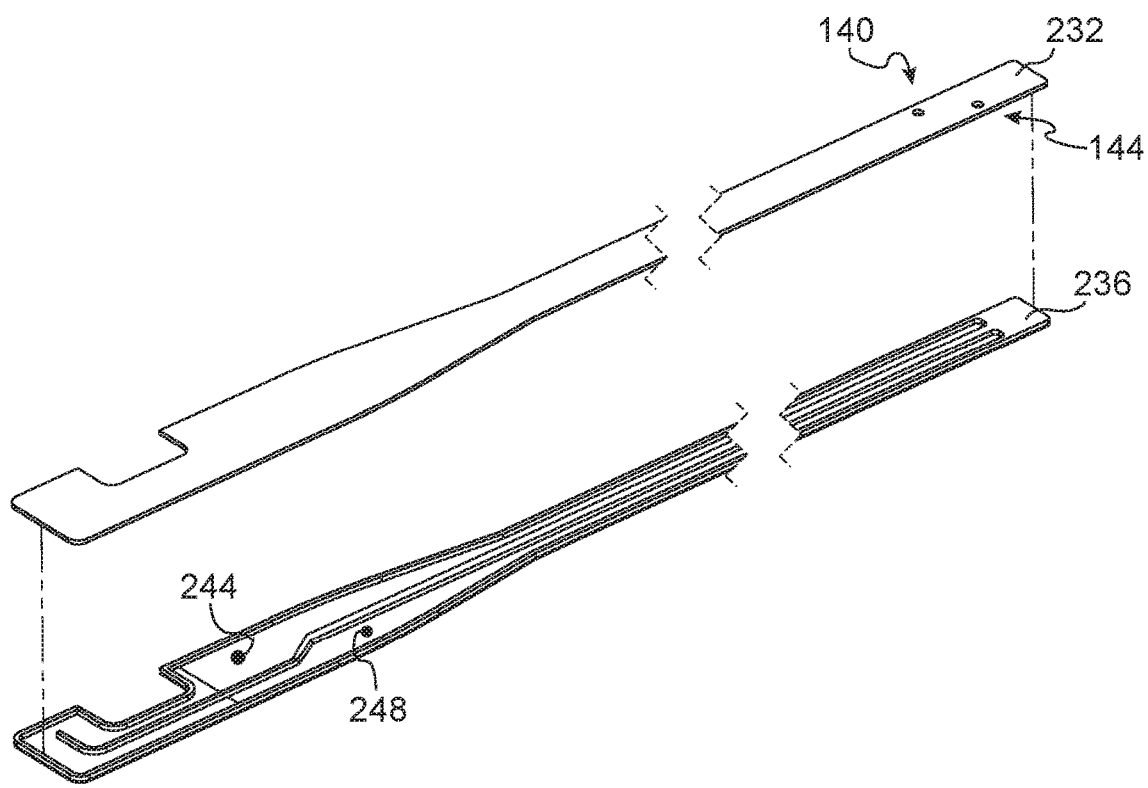
FIG. 22 is an exploded view in perspective of a portion of the embodiment in FIG. 20, partially assembled.

The embodiment generally indicated at 220' in FIG. 20 provides an aperture 136' having a side opening 304 to avoid the issue of penetrating wires passing through a closed aperture and connected at a distal end to one or more electrode. Stated another way: aperture 136' defines an incomplete boundary around the temperature-controlled work area, and includes a side opening 304. In different words, aperture 136' includes a side opening 304 to define a partially bounded conduit extending in a transverse direction through the thickness of the heat transfer mechanism formed in body 224'. Removal of device 220' from an installed position in which temperature of brain tissue is regulated and an installed probe is wired may be effected without cumbersome length-wise wire extraction through the aperture or disconnection of wire distal end(s) from one or more electrode. The device 220' may simply be transversely displaced to pass the connected wire through the side opening.

Figure 26:
FIG. 26 is a bottom plan view of the embodiment in FIG. 24.

Device 220' can be manufactured in substantially the same way as device 220, and the constituent parts are numbered accordingly. Constituent parts that are sufficiently distinguished may be designated with a prime to alert the reader. For example, the surface 308 of encapsulating layer 264 of embodiment 220' is also desirably pulled back from fluid connection structure 140 and 144, and also to resist covering an exposed surface of a heat transfer element 256 (FIG. 26).

While aspects of the invention have been described in particular with reference to certain illustrated embodiments, such is not intended to limit the scope of the invention. The invention for which a monopoly position is currently desired is indicated by the appended claims rather than by the foregoing description. All changes which come within the meaning and range of equivalency of the claims are to be embraced within their scope.

The present invention may be embodied in other specific forms without departing from its spirit or essential characteristics. For one example, one or more element may be extracted from one described or illustrated embodiment and used separately or in combination with one or more element extracted from one or more other described or illustrated embodiment(s), or in combination with other known structure. The described embodiments are to be considered as illustrative and not restrictive. Obvious changes within the capability of one of ordinary skill are encompassed within the present invention.

What is claimed is:

1. An apparatus, comprising:
a heat transfer mechanism comprising an external surface to contact a portion of an exposed surface of a material;
an input conduit in fluid communication with the heat transfer mechanism to direct a working fluid toward an internal surface of the heat transfer mechanism; and
an output conduit in fluid communication with the heat transfer mechanism to direct the working fluid away from the internal surface of the heat transfer mechanism, wherein:
the heat transfer mechanism comprises a gap between heat transfer contact loci, the gap cooperating with the loci to impart a multi-trough cooling temperature profile to the surface of the material, the temperature profile being disposed at a cross-section taken through the gap, wherein:
the gap is associated with an aperture having a length axis and extending through a thickness of the heat transfer mechanism, and;
structure of the aperture defines an incomplete perimeter boundary for a temperature-controlled work area, a complete perimeter boundary of the work area further comprising a side opening of the aperture.

2. The apparatus according to claim 1, further comprising:
a plastically deformable element associated with a portion of the apparatus to permit a user to impart a desired deformed shape to the apparatus.

3. The apparatus according to claim 1, wherein:
the heat transfer mechanism is transversely flexible to conform to the surface.

4. The apparatus according to claim 1, further comprising:
a temperature sensing element associated with the heat transfer mechanism to infer the temperature of a local portion of the material.

5. The apparatus according to claim 1, further comprising:
a catch element to cooperate with a latching anchor to hold the heat transfer mechanism in a desired operable position.

6. An apparatus, comprising:
a heat transfer mechanism comprising an external surface to contact a portion of an exposed surface of a material;
an input conduit in fluid communication with the heat transfer mechanism to direct a working fluid toward an internal surface of the heat transfer mechanism;
an output conduit in fluid communication with the heat transfer mechanism to direct the working fluid away from the internal surface of the heat transfer mechanism, and
the heat transfer mechanism comprises a gap between heat transfer contact loci, the gap cooperating with the loci to impart a multi-trough cooling temperature profile to the surface of the material, the temperature profile being disposed at a cross-section taken through the gap, wherein:
a body portion of the heat transfer mechanism comprises a bonded stack of thin film polymer layers comprising a top layer; a channel layer; and a bottom layer; portions of an input channel and an output channel being disposed in the channel layer and between the top and bottom layers, the input channel and the output channel being constructed such that fluid flow therein wets a portion of said channel layer and a portion of at least one of said top layer and said bottom layer.

7. The apparatus according to claim 6, wherein:
the body portion further comprises an outer encapsulating layer comprising a biocompatible material.

8. The apparatus according to claim 6, wherein:
the gap is associated with an aperture having a length axis and extending through a thickness of the heat transfer mechanism, the aperture comprising a side opening and defining an incomplete perimeter boundary around a temperature-controlled work area.

9. An apparatus, comprising:
a body comprising a top layer, a channel layer, and a bottom layer;
a heat transfer mechanism coupled to the body;
an input channel with an input channel length axis disposed in the channel layer, the input channel being defined in part by walls provided by the channel layer, the top layer, and the bottom layer; and
an output channel with an output channel length axis disposed in the channel layer, the output channel being defined in part by walls provided by the channel layer, the top layer, and the bottom layer; wherein
the heat transfer mechanism comprises an aperture to form a gap between heat transferring elements to impart a multi-trough cooling profile to an object that is cooled by the heat transfer mechanism.

10. The apparatus according to claim 9, wherein:
the aperture comprises a closed perimeter to define a fully bounded conduit extending in a transverse direction through the thickness of the heat transfer mechanism.

11. The apparatus according to claim 9, wherein:
the aperture comprises a side opening to define a partially bounded conduit extending in a transverse direction through the thickness of the heat transfer mechanism.

12. The apparatus according to claim 9, further comprising:
an outer encapsulating layer disposed to cover a portion of the body, the encapsulating layer comprising a biocompatible material.

13. The apparatus according to claim 9, further comprising:
a thermal sensor disposed to indicate a temperature associated with the heat transfer mechanism.

14. The apparatus according to claim 9, further comprising:
a catch element to facilitate holding the heat transfer mechanism in a desired location.

15. The apparatus according to claim 9, further comprising:
a plastically deformable member associated with the body to permit a user to modify a shape of the body.

\* \* \* \* \*